United States Patent [19]

Harsanyi et al.

[11] 4,163,786
[45] Aug. 7, 1979

[54] THIAZOLOISOQUINOLINES WITH CORONARY AND RESPIRATORY EFFECTS

[75] Inventors: Kálmán Harsanyi; Kálmán Takacs; Pál Kiss, all of Budapest; László Szekeres; Gyula Papp, both of Szeged; Eva Benedek, Györ, all of Hungary

[73] Assignee: Chinoin Pharmaceutical and Chemical Works Ltd., Budapest, Hungary

[21] Appl. No.: 869,791

[22] Filed: Jan. 16, 1978

Related U.S. Application Data

[63] Continuation of Ser. No. 701,084, Jun. 30, 1976, abandoned, which is a continuation-in-part of Ser. No. 473,918, May 28, 1974, Pat. No. 3,979,397.

[30] Foreign Application Priority Data

May 30, 1973 [HU] Hungary .............................. CI 1381

[51] Int. Cl.² .................... C07D 513/04; A61K 31/47
[52] U.S. Cl. ...................................... 421/258; 546/80
[58] Field of Search ...... 260/283 S, 288 CF, 287 CF, 260/283 CN, 289 C; 424/258

[56] References Cited

U.S. PATENT DOCUMENTS

| | | | |
|---|---|---|---|
| 2,985,649 | 5/1961 | Lombardino et al. | 260/283 S |
| 3,042,671 | 7/1962 | Lombardino et al. | 260/283 S |
| 3,455,933 | 7/1969 | Gerogiadis et al. | 260/283 S |
| 3,979,397 | 9/1976 | Harsanyi et al. | 260/283 S |

FOREIGN PATENT DOCUMENTS 2426267 9/1975 Fed. Rep. of Germany ....... 260/283 S

OTHER PUBLICATIONS

Harsanyi et al; Chem. Abs. vol 82: 156275x (1975) (Abstract of Ger. Offen. 2,426,267).

*Primary Examiner*—Donald G. Daus
*Assistant Examiner*—Mary C. Lee
*Attorney, Agent, or Firm*—Karl F. Ross

[57] ABSTRACT

The invention relates to new thiazoloisoquinolines of the formula (I), or pharmaceutically acceptable salts thereof,

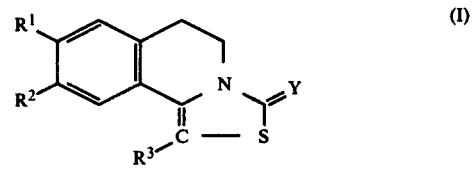

wherein
$R^1$ is hydrogen, hydroxy, alkoxy or aralkoxy,
$R^2$ is hydrogen, hydroxy, alkoxy or aralkoxy,
$R^3$ is hydrogen, cyano, alkyl, aryl, nitro, carboxy, carboalkoxy or carboxamido, and
Y is oxygen, sulfur, or a group of the formula $=N-R^4$, wherein $R^4$ stands for hydrogen, alkyl, aryl, acyl, alkyl-sulfonyl or arysulfonyl.

These new compounds can be used in practice as heart medicines or respiratory analeptics.

6 Claims, No Drawings

THIAZOLOISOQUINOLINES WITH CORONARY AND RESPIRATORY EFFECTS

RELATED APPLICATIONS

This application is a continuation of Ser. No. 701,084 (now abandoned) filed June 30, 1976 as a continuation-in-part of application Ser. No. 473,918 filed May 28, 1974, now U.S. Pat. No. 3,979,397.

This invention relates to new sulfur-containing heterocyclic compounds and pharmaceutical products containing the same, as well as to a method of treatment using these products.

The structure of the new sulfur-containing heterocyclic compounds, termed hereafter briefly as "thiazoloisoquinolines" is given by formula (XII) which also shows the numbering of the ring system.

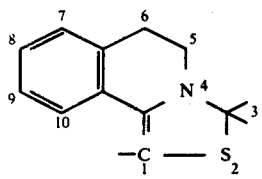

As shown by the above formula, the new ring system encompasses condensed heterocycles. The 3,4-dihydro-1,3-thiazolo[4,3-a]isoquinolines shown in formula (XII) contain a 1,3-thiazole ring condensed with an isoquinoline ring system. These compounds are termed hereafter briefly as "1,3-thiazoloisoquinolines". In these compounds the carbon atom in position 3, with two free valences, is in an oxidation state of 4, i.e. a $C^3$ carbonic acid derivative.

The symbols used in the specification and the claims to define the individual substituents have the following meanings:

$R^1$ is hydrogen, hydroxy, alkoxy or aralkoxy,
$R^2$ is hydrogen, hydroxy, alkoxy or aralkoxy,
$R^3$ is hydrogen, cyano, alkyl, aryl, nitro, carboxy, carboalkoxy or carboxamido,
$R^4$ is hydrogen, alkyl, aryl, acyl, alkylsulfonyl or arylsulfonyl,
$R^5$ is hydrogen, hydroxy, alkoxy or aralkoxy,
$R^6$ is hydrogen, hydroxy, alkoxy or aralkoxy,
$R^7$ is hydrogen, cyano, alkyl, aryl, carboxy, carboalkoxy or carboxamido,
$R^8$ is hydrogen, alkyl, aryl, acyl, alkylsulfonyl or arylsulfonyl,
X is hydrogen, halogen or mercapto,
Y is oxygen, sulfur or $=N-R^4$, and
Y' is oxygen, sulfur or $=N-R^8$.

Where $R^1$ and $R^2$ are alkoxy or aralkoxy, the alkoxy has 1 to 6 and preferably has 1 to 4 carbon atoms. The aryl included in the aralkoxy moiety is either phenyl, 1- or 2-naphthyl, or phenyl or naphthyl substituted by a halo selected from the group consisting of chloro, bromo and iodo and the alkyl has 1 to 6 and preferably 1 to 4 carbon atoms. Where $R^3$ is alkyl it has 1 to 6 and preferably has 1 to 4 carbons; where $R^3$ is aryl it includes phenyl, 1- or 2-naphthyl, or phenyl or naphthyl substituted by a halo selected from the group which consists of chloro, bromo and iodo; where $R^3$ is carboalkoxy, the alkoxy has 1 to 6 and preferably has 1 to 4 carbon atoms, and where $R^2$ is carboxamido, the carboxamido is unsubstituted or the nitrogen atom thereon is mono or disubstituted by alkyl has 1 to 6 and preferably has 1 to 4 carbon atoms. Where Y is $=N-R^4$ and $R^4$ is alkyl, the alkyl had 1 to 6 and preferably 1 to 4 carbon atoms. Where $R^4$ is aryl, the aryl is either phenyl, 1- or 2-naphthyl or phenyl or naphthyl substituted by a halo selected from the group which consists of chloro, bromo and iodo. Where $R^4$ is acyl the acyl group has 1 to 6 and preferably 1 to 4 carbon atoms or the acyl is benzoyl or benzoyl substituted by at least one halogen selected from the group consisting of chlorine, bromine and iodine and finally where $R^4$ is alkylsulfonyl or arylsulfonyl, the alkyl and aryl groups are as defined above.

Where $R^5$ and $R^6$ are alkoxy or aralkoxy, the alkoxy has 1 to 6 and preferably has 1 to 4 carbon atoms. The aryl included in the aralkoxy moiety is either phenyl, 1-naphthyl or 2-naphthyl, or phenyl or naphthyl substituted by halo selected from the group consisting of chloro, bromo and iodo, the alkyl of this moiety having 1 to 6 and preferably 1 to 4 carbon atoms. Where $R^7$ is alkyl it has 1 to 6 and preferably 1 to 4 carbon atoms. Where $R^7$ is aryl, it includes phenyl 1- or 2-naphthyl, or phenyl or naphthyl substituted by halo selected from the group consisting of chloro, bromo and iodo, where $R^7$ is carboalkoxy, the alkoxy has 1 to 6 and preferably 1 to 4 carbon atoms, and where $R^7$ is carboxamido, the carboxamido is unsubstituted or the nitrogen atom thereon is mono or disubstituted by alkyl having 1 to 6 and preferably 1 to 4 carbon atoms. Where $R^8$ is alkyl, the alkyl has 1 to 6 and preferably 1 to 4 carbon atoms. Where $R^8$ is aryl, the aryl is either phenyl, 1-naphthyl or 2-naphthyl or phenyl or naphthyl substituted by halo selected from the group consisting of chloro, bromo and iodo, where $R^8$ is acyl, the acyl group contains from 1 to 6 and preferably 1 to 4 carbon atoms or the acyl is benzoyl or benzoyl substituted by at least one halogen atom selected from the group consisting of chlorine, bromine and iodine and where $R^8$ is alkylsylfonyl or arylsulfonyl, the alkyl and aryl groups are defined above. Finally, where X is halo, the halo is fluoro, chloro, bromo or iodo.

This invention relates to new thiazoloisoquinolines of the formula (I),

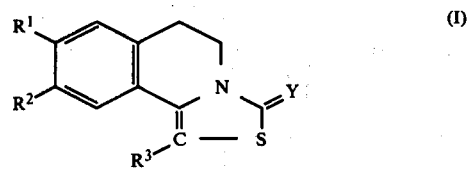

wherein the symbols have the meanings defined above. This invention relates further to pharmaceutical products containing as active ingredient these new compounds, as well as to a process for the preparation of active ingredients.

The compounds of the formula can be prepared according to the invention by reacting a compound of the formula (II)

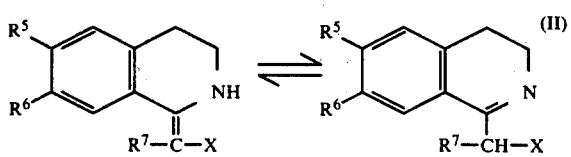

wherein the symbols have the meanings defined above, or a salt thereof with a reactive carbonic acid derivative, provided that at least one of the reactants contains a sulfur atom, and/or by oxidizing an isoquinoline derivative of the formula (III)

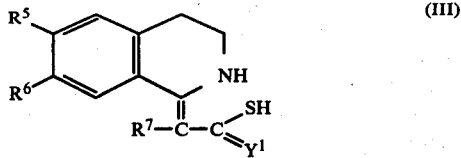

wherein the symbols have the meanings defined above, and/or by converting substituents A', $R^5$, $R^6$ and $R^7$ of the obtained thiazoloisoquinolines of the formula (IA)

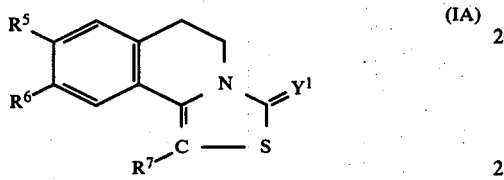

into those required in the end-products. If desired, the obtained thiazoloisoquinolines are converted into their salts, or the compounds of the formula (I) are liberated from the corresponding salts.

The compounds of the formula (I) can be used primarily as pharmaceuticals or intermediates in the production of pharmaceutically active substances. Members of this group exert a very favorable action on the heart musculature, pulmonary circulation and on the oxygen consumption of the heart musculature. The toxicity of these compounds is low. Accordingly, the compounds having the formula (I) can be used as heart medicines and respiratory analeptics.

As shown by formulae (II), (IV), (VI), (VII) and (VIII).

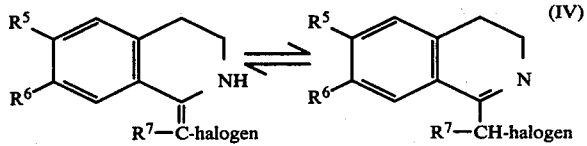

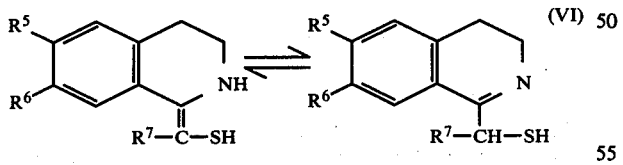

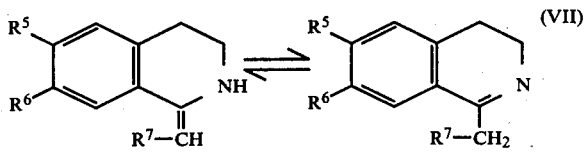

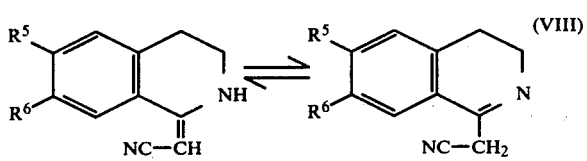

all compounds of these groups may exist in at least two tautomeric forms. The scope of the invention extends to all of these tautomers and tautomeric mixtures.

The carbonic acid-type reagent is chosen according to the substituent of the side chain attached to position 1 of the isoquinoline having the formula (II), and according to the substituent required in position 3 of the condensed ring system of the intermediate having the formula (IA). Thus, e.g. rhodanides, halocyanides, mono-thiocarbonic acid esters, thioureas, xanthates, cyanamides, acylisothiocyanates, carbon disulfide, etc. can be used as carbonic acid-type reagent. If desired, these reagents can be formed directly in the reaction medium from the appropriate precursors.

According to one method of the invention an isoquinoline of the formula (IV), i.e. a compound containing a halogen-substituted side chain in position 1, is used as starting substance. This compound can be reacted with carbonic acid derivatives in various ways, to yield the compounds of the formula (IA) either directly or via one or more other intermediates.

Condensed 1,3-thiazoloisoquinolines can be prepared directly from the compounds of the formula (IV) by racting them with sulfur-containing carbonic acid derivatives capable of S-anion formation. These carbonic acid derivatives are reacted preferably in the form of their alkali metal, alkaline earth metal or ammonium salts. As carbonic acid derivatives, e.g. rhodanides, xanthates, salts of monothiocarbonic acid hemiesters, etc. can be used.

The reaction is carried out preferably in an alcohol or in another protic solvent, such as a formamide. As solvents, however, dipolar aprotic substances, e.g. dimethylformamide, dimethylsulfoxide, or hexamethylphosphoric acid triamide can also be used.

The reaction temperature is adjusted in accordance with the solvent used. If a solvent with a boiling point lower than 100° C. is used as the reaction medium, the reaction is carried out at the boiling point of the system, whereas, when solvents of higher boiling points are used, the reaction temperature is between 80° and 120° C.

The products can be separated in crystalline form from the solvent, using optionally another solvent as precipitant.

As starting substances of the formula (IV) the ones containing a bromine substituent in the side chain are utilized preferably. These compounds can be prepared easily by the bromination of the appropriately substituted 1-methylene-1,2,3,4-tetrahydroisoquinolines. According to a preferred method of the invention the obtained isoquinoline derivative containing a halogen-substituted side chain is reacted further directly in the medium where it has been prepared, i.e. without isolation.

When reacting isoquinolines of the formula (IV) with other sulfur-containing carbonic acid derivatives, sulfur-containing isoquinoline intermediates of the formulae (III) or (VI) are obtained in one or more steps.

Thus, the salts of the mercapto-isoquinolines of the formula (VI) can be prepared by reacting an isoquinoline of the formula (IV) with thiourea, and decomposing the obtained isothiuronium salt with an alkali. The obtained mercaptides represent a subgroup of the starting substances having the formula (II), offering subsequent reactions described below.

When reacting the compounds of the formula (IV) with sodium thiosulfate, again isoquinolines of the formula (VI) are obtained via the appropriate Bunte's salts.

The reaction of the isoquinolines of the formula (VI), containing a mercapto group in the side chain, with a halocyanide, phosgene, thiophosgene, chloroformate or chlorothioformate yields directly the appropriately substituted 1,3-thiazoloisoquinolines.

The conditions of these reactions depend on the reactants utilized. The reactants are generally given to the aqueous solution of the appropriate alkali metal salt of the thiolate. If the hydrolyzability of the reactant does not permit carrying out the reaction in an alkaline medium, the reaction is carried out in a well-stirred two-phase system. As water-immiscible solvents, preferably hydrocarbons or chlorinated organic solvents are used. In other cases dipolar aprotic solvents, e.g. dimethylformamide can be used to advantage. The reactions are in general carried out at low temperatures.

Similarly, the end-products can be obtained via intermediates by reacting the compounds of the formula (IV), in the form of the corresponding Grignard-reagents, with carbon disulfide. The Grignard-reagent can be prepared in ether-type solvents, such as in diethyl ether, dioxane or tetrahydrofuran.

According to a further method of the invention isoquinolines of the formula (VII), constituting a subgroup of the compounds having the formula (II), are used as starting substances. These compounds can be reacted with sulfur-containing carbonic acid derivatives to yield the sulfur-containing isoquinolines, optionally via one or more intermediates.

Thus, for instance, the compounds of the formula (VII) can be reacted with acylisothiocyanates to yield the corresponding isoquinolines containing an N-acylimino substituent in the side chain. The acyl group of these substances can be split off, if desired. These acylated or deacylated intermediates can be used for the preparation of 1,2-thiazoloisoquinolines containing an imino or =N-acyl substituent in position 2 of the condensed ring system. In this latter case the acyl substituent attached to the nitrogen atom may be benzoyl, alkylsulfonyl or arylsulfonyl.

The reaction with acylisothiocyanates is carried out preferably in acetone, chlorinated solvents, ketones, lower nitriles and, ethers.

According to still a further method aspect of the invention the isoquinolines of the formula VIII, ($R^3$=cyano or nitrilo) containing a cyanomethylene side chain and constituting a subgroup of the compounds having the formula (VII), are reacted with hydrogen sulfide to yield the thiocarbamoyl-substituted intermediates of the formula (IX).

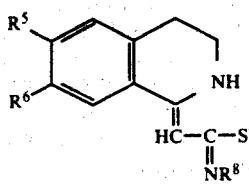

These latter compounds can be oxidized to yield the corresponding 1,2-thiazoloisoquinolines. The reaction with hydrogen sulfide is carried out preferably by introducing hydrogen sulfide gas into the system at 0° to 50° C., in the presence of a basic substance, e.g. triethylamine, piperidine or, preferably, pyridine. The addition of hydrogen sulfide can be speeded up by the use of higher temperature in a closed vessel.

By reacting the compounds of the formula (VII) with ethyl magnesium bromide, a trans-Grignard reaction can also be carried out. During this reaction ethane is evolved, which is removed from the system by heating. The reaction is carried out preferably in toluene, in the presence of a small amount of ether. The reaction of the obtained reagent with carbon disulfide also leads to the intermediates of the formula (III), containing a dithiocarboxy substituent in the side chain.

The compounds of the formula (VII) that contain a carbonylchloride substituent in the side chain can be converted into the isoquinolines of the formula (X) in a reaction with sodium hydrosulfide.

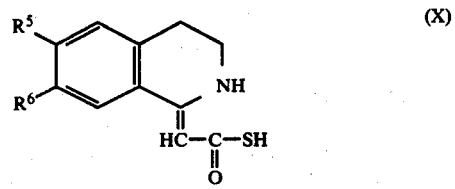

The compounds of the formula (X), containing a thiocarboxy substituent in the side chain, constitute a subgroup of the compounds having the formula (III).

The oxidation can be carried out preferably with a halogen in the presence of an acid binding agent. Thus, for example, the reaction can be carried out with iodine or bromine in the presence of pyridine, quinoline, picoline, lutidine, etc. The reaction is in general conducted at a temperature of about 50° C.

It will be obvious to one skilled in the art that the carbonic acid derivatives used as reactants are selected generally in accordance with the desired substituents of the 1,3-thiozoloisoquinoline and end-products.

Thus, for example, a compound containing an imino group in position 3 of the condensed ring system can be obtained in a reaction with a rhodanide or halocyanide. O-Alkylmonothiocarbonate salts as reactants lead to the oxygen-substituted products, whereas alkyl xanthates to the corresponding sulfur-substituted compounds.

Once the thiazoloisoquinoline ring system is built up, the substituent groups introduced during ring closure can be converted into other groups, and thus the compounds of the formula (IA) can be converted into the compounds of the formula (I).

Thus, for example, the hydroxy groups attached to positions 8 and 9, respectively, can be alkylated or aralkylated, or the alkoxy or aralkoxy groups can be converted into hydroxy substituents. The ether bond can be split by hydrogen halides, pyridine hydrochloride, etc. Alkoxy- and aralkoxy groups can be formed by reacting the hydroxy compounds with appropriate alkyl or aralkyl halides or sulfates in the presence of an acid binding agent. The ether bond of the benzyloxy derivatives can also be split by catalytic hydrogenation. In the alkoxy or aralkoxy groups the alkyl chain may contain preferably 1 to 4 carbon atoms, and the most preferred aralkyl group is benzyl.

The thiazoloisoquinolines containing a side-chain in position 1 to which a group derived from a carbonic acid is attached can be converted into the corresponding compounds containing a carboxy substituent in the side chain.

The nitrile group in position 1 of the ring system can be converted into an acid amide or carboxy group by treatment with an acid. In this reaction preferably sulfuric acid is applied. The nitrile group in position 1 can also be converted into a carboxy group by treatment with a base. Alternately, the nitrile group can be converted into a carbalkoxy group by acid-catalyzed alcoholysis. In turn, the acid amide group can be dehydrated with phosphorous pentoxide, phosphorous oxychloride or thionyl chloride to yield the corresponding nitrile-substituted compounds. The nitrile group can also be converted into an acid amide group by treatment with a concentrated acid (e.g. sulfuric or polyphosphoric acid) or with an alkaline hydrogen peroxide solution.

The compounds that contain a carboxy group in position 1 of the condensed ring system can be esterified with alcohols in proton-catalyzed reactions. Alternatively, these compounds can be decarboxylated by heating.

The compounds wherein the side chain attached to position 1 of the ring system contains a methyl group can be converted into the corresponding carboxy substituted compounds by oxidation with potassium permanganate. The imino groups attached to position 3 of the condensed ring system can be alkylated with known alkylating agents, preferably after salt-formation with a strong base. For this purpose sodium alcoholates, sodium amide or sodium hydride can be used. N-acylation can be carried out in a pyridine medium with various acylating agents, e.g. carboxylic chlorides, aryl or acylsulfonic acid chlorides, etc. The acyl group of the N-acylimino groups attached to position 3 of the condensed ring system can be removed by acid hydrolysis.

The condensed-ring compounds containing an imino group can be racted with amine salts to yield the corresponding N-substituted derivatives. This reaction is carried out preferably in dimethylformamide, at the boiling point of the solvent.

The basic compounds of the formula (I) can be converted into their salts by reacting them with mineral or organic acids, e.g. sulfuric, hydrochloric, phosphoric, nitric, acetic, rhodanic, propionic, lactic, malic, citric, succinic, maleic, fumaric, ethanedisulfonic, benzoic, salicyclic, aspartic, etc. acids. Using polybasic acids, acidic salts can be formed as well.

The compounds of the formula (I) can be converted into pharmaceutical products, e.g. tablets, coated tablets, suppositories, capsules, solutions and powders, injectable preparations. These compositions may contain the active agents as such, or in admixture with carriers, diluents and/or other additives.

In order to demonstrate the biological activity of the compounds according to the invention, the pharmacological data of 1-cyano-3-imino-3,4,5,6-tetrahydro-8,9-dimethoxy-1,3-thiazolo[4,3-a]isoquinoline (referred to hereinafter as compound "A") are listed below. The other compounds included herein also possess the biological activity of compound "A".

Compound "A", administered in a dosage of 200 γ/kg increases the contractility of the heart musculature by 24% for 71 minutes, whereas when administering Carbochromen, (3-[beta-2-diethylaminoethyl]-4-methyl-7-[carbethoxymethoxy]-2-oxo-1,2-chromen) in a dosage of 2 mg./kg., the same effect lasts only for 55 minutes.

Compound "A", administered in a dosage of 100 γ/kg. into narcotized dogs, increases the cardiac output by 30%, and this effect lasts for 1.5 hours. In contrast, Carbochromen, administered in a dosage of 2 mg./kg., causes an increase of 25% and the effect lasts for 50 minutes.

Compound "A", administered in a dosage of 200 γ/kg., decreases the total peripheral resistance by 37% for 1.75 hours, whereas a 4 mg./kg. dosage of Carbochromen causes a decrease of 33% only for one hour.

Compound "A", administered in a dosage of 100 γ/kg., decreases the pulmonary circulation resistance by 25% for one hour. A similar effect cannot be attained with the known agents.

Compound "A", administered in a dosage of 200 γ/kg., increases the coronary flow by 30% for 1.5 hours. In contrast, the known coronary dilatants produce this effect in much higher dosages and for much shorter periods (10 to 60 minutes).

Compound "A", administered in a dosage of 200 γ/kg. into narcoticized dogs, decreases the oxygen consumption of the left ventricle by 20%, and this effect lasts for one hour. In contrast, Carbochromen does not exert such a prolonged effect even in a tenfold dosage.

On this basis, compound "A", administered in a dosage of 200 γ/kg., increases the heart efficiency by 42%.

From the therapeutical indices, compound "A" appears to be 13.6 times more active than Carbochromen with respect to coronary flow, and 44 times more active with respect to the coronary resistance. Compound "A" increases significantly the flow and decreases the resistance for both the femoral and the carotid vessels.

The fact that the above presented increase in total coronary flow after Compound "A" is also reflected by a corresponding increase in the nutritional circulation of the myocardium as estimated by the $H_2$-washout method. The results show that the lasting effect of the drug on the coronary flow is a useful action providing for a better oxygen supply of the myocardial fibers and is not due to some shunting mechanism.

It can be also seen that after coronary occlusion the drug may temporarily improve the blood supply to the ischemic area, whereas in the non-infarcted area in the first 15 minutes after treatment, the drug induced increase is even somewhat higher than in the same area without occlusion.

Usefulness of Compound "A" as a potential antianginal drug is demonstrated by further experiments according to which it could significantly reduce the ischemic ST-segment elevation in the specific, effort type antianginal test, consisting of a combination of coronary constriction and cardiac overload induced by pacing. Similar effectiveness could be shown against pituitrin-induced T wave elevation in rats.

The drug exerts its effect also when administered by introduodenal route. 5 mg./kg. i.d. dosage evoked a marked increase in myocardial nutritional circulation, reaching values up to 30% and lasting for more than 3 hours. However the drug was active already in oral doses as low as 1 and 2 mg./kg. shown by the inhibition of the pituitrin induced elevation of the T wave in rats.

The invention is elucidated in detail by the aid of the following non-limiting Examples.

EXAMPLE 1

0.7 g. of potassium rhodanide are dissolved in 20 ml. of hot dry alcohol, and 0.9 g. of 1-chloromethyl-6,7-dimethoxy-3,4-dihydro-isoquinoline hydrochloride are added to the boiling solution within 30 minutes. The reaction mixture is refluxed for 3 hours, thereafter the solvent is evaporated, and the residue is admixed with water. 0.9 g. of 3-imino-8,9-dimethoxy-3,4,5,6-tetrahydro-1,3-thiazolo[4,3-a]isoquinoline rhodanide are obtained; m.p.: 220° C. (after recrystallization from 96% alcohol).

Analysis: Calculated for $C_{14}H_{15}N_3S_2O_2$ (M=321.42): C: 52.28%, H: 4.70%, N: 13.07%, S: 19.96%. Found: C: 51.88%, H: 4.68%, N: 13.13%, S: 19.67%.

1.0 g. of the above salt is dissolved in 20 ml. of hot water, and the solution is rendered alkaline with 10% sodium hydroxide solution. Upon cooling, 0.8 g. of 3-imino-8,9-dimethoxy-3,4,5,6-tetrahydro-1,3-thiazolo[4,3-a]isoquinoline separates in crystalline state. M.p.: 145° C. (after recrystallization from a mixture of petroleum ether and benzene)

Analysis: Calculated for $C_{13}H_{14}N_2O_2S$ (M=262.32): C: 59.52%, H: 5.38%, N: 10.68%, S: 12.22%. Found: C: 59.50%, H: 5.12%, N: 10.66%, S: 11.93%.

0.5 g. of the above salt are dissolved in the mixture of 10 ml. of water and 1 ml. of concentrated hydrochloric acid by heating; the solution is filtered when hot, and allowed to cool. 0.5 g. of 3-imino-8,9-dimethoxy-3,4,5,6-tetrahydro-1,3-thiazolo[4,3-a]isoquinoline hydrochloride separates in a crystalline state; m.p.: 272°-274° C. under decomposition (after recrystallization from 96% alcohol).

Analysis: Calculated for $C_{13}H_{15}N_2O_2SCl$ (M=298.79): C: 52.29%, H: 5.06%, N: 9.38%, S: 10.73%, Cl: 11.87%. Found: C: 52.11%, H: 5.16%, N: 9.65%, S: 10.70%, Cl: 11.60%.

EXAMPLE 2

According to a preferred method of the invention 1-cyanomethylene-1,2,3,4-tetrahydro-6,7-dimethoxy-isoquinoline is brominated and reacted with rhodanide in a single step.

57.5 g. (0.25 moles) of 1-cyanomethylene-1,2,3,4-tetrahydro-6,7-dimethoxy-isoquinoline, 21.5 g. (0.255 moles) of sodium hydrocarbonate and 375 ml. of methanol are introduced into a 2 l. flask equipped with a stirrer, reflux condenser, thermometer and addition funnel. The mixture is heated to boiling with stirring, thereafter it is cooled to 60° C., and 40 g. (0.25 moles) of bromine are added dropwise to the solution within 20 minutes. During the addition carbon dioxide evolves and leaves the system. Thereafter the solution is boiled, and a solution of 40 g. (about 0.4 moles) of potassium rhodanide in 300 ml. of methanol is added. The separated precipitate temporarily dissolves, thereafter a loose, voluminous precipitate separates. The mixture is boiled for 1.5 hours, thereafter left to stand in a refrigerator overnight. The precipitate is filtered off, suspended in 500 ml. of water, and 20 ml. of 1 N sodium hydroxide solution are added to the suspension. The precipitate is filtered again, and washed with 3×100 ml. of water. 62.3 g. (86.8%) of 1-cyano-3-imino-3,4,5,6-tetrahydro-8,9-dimethoxy-1,3-thiazolo[4,3-a]isoquinoline are obtained; m.p.: 229°-230° C. (decomposition).

EXAMPLE 3

4.0 g. of potassium rhodanide are dissolved in 200 ml. of hot dry alcohol, and 8.0 g. of 1-(α-bromo)-cyanomethylene-6,7-dimethoxy-1,2,3,4-tetrahydro-1-isoquinoline are added to the boiling solution within 30 minutes. The mixture is refluxed for an additional 4 hours, thereafter the solvent is evaporated in vacuo, and the residue is triturated with water. In this way 7.1 g. of crystalline 1-cyano-3-imino-3,4,5,6-tetrahydro-8,9-dimethoxy-1,3-thiazolo[4,3-a]isoquinoline are obtained; m.p.: 236° C. (after recrystallization from butanol).

Analysis: Calculated for $C_{14}H_{13}N_3O_2S$ (M=287.33): C: 58.52%, H: 4.63%, N: 14.63%, S: 11.16%. Found: C: 58.20%, H: 4.45%, N: 14.64%, S: 11.16%.

EXAMPLE 4

2.0 g. of S-(α-cyano-α-6,7-dimethoxy-3,4-dihydro-1-isoquinolyl)-methyl-isothiuronium bromide (prepared from 1-(α-bromo)-cyanomethylene-6,7-dimethoxy-1,2,3,4-tetrahydroisoquinoline with thiourea; m.p.: 187° C. under decomposition) are dissolved in 20 ml. of hot 50% alcohol. 5 ml. of 10% sodium hydroxide solution are added, and the mixture is refluxed for 15 minutes. Thereafter a solution of 0.5 g. of cyanogen bromide in 5 ml. of alcohol is added, and the mixture is boiled for an additional 0.5 hours. The solvent is evaporated in vacuo, and the residue is triturated with water. 1.35 g. of 1-cyano-3-imino-3,4,5,6-tetrahydro-8,9-dimethoxy-1,3-thiazolo[4,3-a]isoquinoline are obtained; m.p.: 229°-230° C. (under decomposition).

EXAMPLE 5

150 mg. of potassium rhodanide are dissolved in 5 ml. of hot dry alcohol, and 360 mg. of 1-(α-bromo)-cyanomethylene-6,7-diethoxy-1,2,3,4-tetrahydro-1-isoquinoline are added to the solution. The mixture is refluxed for 3 hours, then evaporated to dryness. The residue is triturated with water. 220 mg. of 1-cyano-3-imino-8,9-diethoxy-3,4,5,6-tetrahydro-1,3-thiazolo[4,3-a]isoquinoline are obtained; m.p.: 180°-182° C. under decomposition (after recrystallization from butanol).

Analysis: Calculated for $C_{16}H_{17}N_3O_2S$ (M=315.39): C: 60.93%, H: 5.43%, N: 13.32%, S: 10.17%. Found: C: 60.92%, H: 5.49%, N: 13.18%, S: 10.00%.

EXAMPLE 6

0.75 g. of O-ethyl-monothiocarbonate potassium salt (Renders' salt) are dissolved in 15 ml. of hot dry alcohol, and 1.55 g. of 1-(α-bromo)-1-cyanomethylene-6,7-dimethoxy-1,2,3,4-tetrahydro-1-isoquinoline are added to the boiling solution. The mixture is refluxed for one hour, thereafter the solvent is evaporated, and the residue is triturated with water. 1.0 g. of 1-cyano-8,9-dimethoxy-3,4,5,6-tetrahydro-1,3-thiazolo[4,3-a]isoquinoline-3-one are obtained; m.p.: 205°-207° C. (after recrystallization from butanol).

Analysis: Calculated for $C_{14}H_{12}N_2O_3S$ (M=288.32): C: 58.32%, H: 4.19%, N: 9.72%, S: 11.12%. Found: C: 58.30%, H: 4.17%, N: 9.90%, S: 11.26%.

EXAMPLE 7

250 mg. of O-ethyl monothiocarbonate potassium salt are dissolved in 15 ml. of hot dry alcohol, and 600 mg. of 1-(α-bromo)-cyanomethylene-6,7-diethoxy-1,2,3,4-tetrahydro-1-isoquinoline are added to the solution. The mixture is refluxed for 2 hours, thereafter the solvent is evaporated, and the residue is triturated with water. 420 mg. of 1-cyano-8,9-diethoxy-3,4,5,6-teyrahydro-1,3-thiazolo[4,3-a]isoquinoline-3-on are obtained; mp.: 172°-174° C. (after recrystallization from butanol).

Analysis: Calculated for $C_{16}H_{16}N_2O_3S$ (M=316.37): C: 60.74%, H: 5.09%, N: 8.86%, S: 10.13%. Found: C: 60.51%, N: 4.93%, N: 8.60%, S: 9.79%.

EXAMPLE 8

0.6 g. of potassium ethyl xanthate are dissolved in 8 ml. of hot dry alcohol, and 1.0 g. of 1-(α-bromo)- cyanomethylene-6,7-dimethoxy-1,2,3,4-tetrahydro-1-isoquinoline are added to the boiling solution. The mixture is refluxed for 0.5 hours, thereafter the solvent is evaporated, and the residue is triturated with water. 0.85 g. of 1-cyano-8,9-dimethoxy-3,4,5,6-tetrahydro-1,3-thiazolo[4,3-a]isoquinoline-3-thione are obtained; m.p.: 228° C. (after recrystallization from butanol).

Analysis: Calculated for $C_{14}H_{12}N_2O_2S_2$ (M=304.38): C: 55.24%, H: 3.97%, N: 9.20%, S: 21.07%. Found: C: 55.40%, H: 4.08%, N: 9.26%, S: 21.30%.

EXAMPLE 9

2.0 g. of potassium rhodanide are dissolved in 30 ml. of hot dry alcohol, and a solution of 2.0 g. of 1-(α-bromo)-ethyl-6,7-dimethoxy-3,4-dihydro-1-isoquinoline hydrochloride (Arch, der Pharm. 277, 177 (1939)) in 10 ml. of dry alcohol is added dropwise to the boiling solution. The mixture is refluxed for 2 hours, thereafter the solvent is evaporated, and the residue is triturated with water. 1.8 g. of 1-methyl-3-imino-8,9-dimethoxy-3,4,5,6-tetrahydro-1,3-thiazolo[4,3-a]-isoquinoline rhodanide are obtained; m.p.: 218°–220° C. (after recrystallization from dry alcohol).

Analysis: Calculated for $C_{15}H_{17}N_3O_2S_2$ (M=335.44): C: 53.71%, H: 5.11%, N: 12.53%, S: 19.12%. Found: C: 54.02%, H: 5.33%, N: 12.65%, S: 19.29%.

0.5 g. of the above salt are admixed with 10 ml. of hot water, and the mixture is rendered alkaline with 10% sodium hydroxide solution. Upon cooling, 0.42 g. of 1-methyl-3-imino-8,9-dimethoxy-3,4,5,6-tetrahydro-1,3-thiazolo[4,3-a]isoquinoline separates in crystalline state; m.p.: 145°–147° C. (after recrystallization from alcohol).

Analysis: Calculated for $C_{14}H_{16}N_2O_2S$ (M=276.35): C: 60.84%, H: 5.83%, N: 10.14%, S: 11.60%. Found: C: 61.12%, H: 6.04%, N: 10.02%, S: 11.82%.

EXAMPLE 10

10 ml. of toluene and 2.0 ml. of phosphorous oxychloride are added to 2.0 g. of N-(α-chloro-phenylacetyl)-homoveratrylamine (prepared from homoveratrylamine with α-chloro-phenylacetylchloride; m.p.: 107°–109° C.), and the mixture is refluxed for 2 hours. The mixture is evaporated to dryness in vacuo, the residue is dissolved in 10 ml. of dry alcohol, and this solution is again evaporated to dryness. The residue is dissolved in 10 ml. of dry alcohol, and this solution is added dropwise to the hot solution of 2.0 g. of potassium rhodanide in 40 ml. of dry alcohol. The mixture is refluxed for 2 hours, thereafter evaporated to dryness, and the residue is triturated with water. 1.1 g. of 1-phenyl-3-imino-8,9-dimethoxy-3,4,5,6-tetrahydro-1,3-thiazolo[4,3-a]isoquinoline rhodanide are obtained; m.p.: 181°–183° C. (after recrystallization from dry alcohol).

Analysis: Calculated for $C_{20}H_{19}N_3O_2S_2$ (M=397.51): C: 60.43%, H: 4.82%, N: 10.57%, S: 16.13%. Found: C: 60.40%, H: 5.15%, N: 10.44%, S: 16.40%.

1.0 g. of the above salt is admixed with 6 ml. of alcohol; the mixture is rendered alkaline with 10% sodium hydroxide solution, thereafter the mixture is diluted with 6 ml. of water. 0.8 g. of 1-phenyl-3-imino-8,9-dimethoxy-3,4,5,6-tetrahydro-1,3-thiazolo[4,3-a]isoquinoline are obtained; m.p. 123°–125° C. (after recrystallization from 50% alcohol).

Analysis: Calculated for $C_{19}H_{18}N_2O_2S$ (M=338.42): C: 67.43%, H: 5.36%, N: 8.28%, S: 9.48%. Found: C: 67.13%, H: 5.26%, N: 8.34%, S: 9.34%.

1.0 g. of the above base is dissolved in 5 ml. of dry alcohol, and the solution is acidified with dry alcoholic hydrochloric acid. 0.75 g. of 1-phenyl-3-imino-8,9-dimethoxy-3,4,5,6-tetrahydro-1,3-thiazolo[4,3-a]isoquinoline hydrochloride are obtained; m.p. 264°–266° C. under decomposition (after recrystallization from dry alcohol).

Analysis: Calculated for $C_{19}H_{19}N_2O_2SCl$ (M=374.88): C: 60.87% H: 5.11% N: 7.47% S:8.55% Cl: 9.46%. Found: C: 60.55% H: 5.20% N: 7.55% S: 8.70% Cl: 9.64%.

EXAMPLE 11

1.0 g. of 1-cyano-3-imino-8,9-dimethoxy-3,4,5,6-tetrahydro-1,3-thiazolo[4,3-a]isoquinoline is added portionwise to 3.0 ml. of concentrated sulfuric acid with stirring, and the reaction mixture is allowed to stand at room temperature overnight. The mixture is poured onto ice and rendered alkaline. 0.75 g. of 1-carboxamido-3-imino-8,9-dimethoxy-3,4,5,6-tetrahydro-1,3-thiazolo[4,3-a]isoquinoline are obtained; m.p: 240° C. (after recrystallization from 75% alcohol).

Analysis: Calculated for $C_{14}H_{15}N_3O_3S$ (M=305.35): C: 55.06%, H: 4.95%, N: 13.76%, S: 10.50%. Found: C: 54.88%, H: 5.05%, N: 13.77%, S: 10.17%.

1.0 g. of the above product is dissolved in the hot mixture of 9 ml. of water and 1 ml. of concentrated hydrochloride acid, and the solution is filtered when hot. Upon cooling, 0.8 g. of crystalline 1-carboxamido-3-imino-8,9-dimethoxy-3,4,5,6-tetrahydro-1,3-thioazolo[4,3-a]isoquinoline hydrochloride hemihydrate separates from the filtrate; m.p.: 270°–272° C. (under decomposition).

Analysis: Found: C: 47.52%, H: 4.84%, N: 11.77%, S: 9.48%, Cl: 9.89%. Calc. C: 47.93%, H: 4.88%, N: 11.98%, S: 9.14%, Cl: 10.11%. Empirical formula: $C_{14}H_{16}N_3O_3SCl.\frac{1}{2}H_2O$ (M=350.82).

EXAMPLE 12

10 ml. of 10% sodium hydroxide solution and 20 ml. of alcohol are added to 1.0 g. of 1-cyano-3-imino-8,9-dimethoxy-3,4,5,6-tetrahydro-1,3-thiazolo[4,3-a]isoquinoline, and the mixture is refluxed for 6 hours. The alcohol is distilled off, and the residue is neutralized to pH 7 to 8 with hydrochloric acid. 0.8 g. of 1-carboxy-3-imino-8,9-dimethoxy-3,4,5,6-tetrahydro-1,3-thiazolo[4,3-a]isoquinoline monohydrate are obtained; m.p.: 177°–179° C. (after recrystallization from 50% alcohol).

Analysis: Calculated for $C_{14}N_{16}N_2O_5S$ (M=324.35): C: 51.84%, H: 4.97%, N: 8.64%, S: 9.88%. Found: C: 51.64%, H: 4.83%, N: 8.56%, S: 10.02%.

EXAMPLE 13

A mixture of 2.87 g. (0.01 moles) of 1-cyano-3-imino-3,4,5,6-tetrahydro-8,9-dimethoxy-1,3-thiazolo[4,3-a]isoquinoline, 1.7 g. (about 0.01 moles) of p-chloro-aniline hydrochloride and 30 ml. of dimethylformamide is refluxed for 10 hours. The precipitate separted oncooling is filtered off. 2.1 g (53%) of 1-cyano-3-(N-p-chlorophenyl)-imino-3,4,5,6-tetrahydro-8,9-dimethoxy-1,3-thiazolo[4,3-a]isoquinoline are obtained: m.p.: 254° C. (after recrystallization from dichloromethane).

Analysis: Calculated for $C_{20}H_{16}N_3O_2SCl$ (M=397.88): N: 10.56%, Cl: 8.91%. Found: N: 10.40%, Cl: 9.26%.

EXAMPLE 14

5 ml. of pyridine and 0.5 ml. of acetic anhydride are added to 0.5 g. of 1-cyano-3-imino-8,9-dimethoxy-3,4,5,6-tetrahydro-1,3-thiazolo[4,3-a]isoquinoline, and the reaction mixture is refluxed for 0.5 hours. The mixture is cooled and diluted with water. 0.6 g. of 1-cyano-3-acetimino-8,9-dimethoxy-3,4,5,6-tetrahydro-1,3-thiazolo[4,3-a]isoquinoline are obtained; m.p.: 223°–225° C. (after recrystallization from butanol).

Analysis: Calculated for $C_{16}H_{15}N_3O_3S$ (M=329.37): C: 58.34%, H: 4.59%, N: 12.76%, S: 9.74%. Found: C: 58.50%, H: 4.50%, N: 13.02%, S: 10.08%.

EXAMPLE 15

5 ml. of pyridine and 0.3 ml. of benzoyl chloride are added to 0.5 g. of 10-cyano-3-imino-8,9-dimethoxy-3,4,5,6-tetrahydro-1,3-thiazolo[4,3-a]isoquinoline, and the mixture is refluxed for 0.5 hours. After cooling, the mixture is diluted with water. 0.6 g. of 1-cyano-3-benzoylimino-8,9-dimethoxy-3,4,5,6-tetrahydro-1,3-thiazolo[4,3-a]isoquinoline is obtained in crystalline state; m.p.: 274°–276° C. (after crystallization from a mixture of dimethylformamide and butanol).

Analysis: Calculated for $C_{21}H_{17}N_3O_3S$ (M=391.43): C: 64.43%, H: 4.37% N: 10.74%, S: 8.19%. Found: C: 64.73%, H: 4.37%, N: 10.93%, S: 8.48%.

EXAMPLE 16

A mixture of 2.87 g. (0.01 moles) of 1-cyano-3-imino-3,4,5,6-tetrahydro-8,9-dimethoxy-1,3-thiazolo[4,3-a]isoquinoline, 1.2 g. of aminoethanol hydrochloride and 30 ml. of dimethylformamide is refluxed for 10 hours. The solution is evaporated, and the residue is crystallized from nitromethane. 1-Cyano-3-(N-2-hydroxyethyl)-imino-3,4,5,6-tetrahydro-8,9-dimethoxy-1,3-thiazolo[4,3-a]isoquinoline, melting at 202°–204° C., is obtained.

Analysis: Calculated for $C_{16}H_{17}N_3O_3S$ (M=331.39): C: 57.99%, H: 5.17%, N: 12.68%. Found: C: 57.79%, H: 4.93%, N: 12.72%.

EXAMPLE 17

0.5 g. of potassium rhodanide are dissolved in 35 ml. of hot dry alcohol, and 1.0 g. (0.003 moles) of 1-(α-bromo)-nitromethylene-6,7-dimethoxy-1,2,3,4-tetrahydro-isoquinoline is added to the boiling solution within 20 minutes. The mixture is refluxed overnight. 0.75 g. of 1-nitro-3-imino-8,9-dimethoxy-3,4,5,6-tetrahydro-1,3-thiazolo[4,3-a]isoquinoline are obtained; m.p.: 220°–221° C. (after recrystallization from dry alcohol).

Analysis: Calculated for $C_{13}H_{13}N_3O_4S$ (M=307.33): C: 50.81%, H: 4.26%, N: 13.67%, S: 10.43%. Found: C: 51.05%, H: 4.17%, N: 13.53%, S: 10.25%.

EXAMPLE 18

0.66 g. (0.002 moles) of 1-cyano-3-imino-8,9-dihydroxy-1,2,3,4-tetrahydro-1,3-thiazolo[4,3-a]isoquinoline hydrochloride dihydrate are dissolved in 20 ml. of hot 50% alcohol, and 3.0 ml. of 10% sodium hydroxide solution are added to the mixture, 1 to 2 minutes thereafter 1.0 ml. of methyl iodide are added, and the mixture is refluxed for 3 hours. The crystalline precipitate separated upon cooling is filtered off, washed with 50% alcohol and dried, 0.4 g. of 1-cyano-3-imino-8,9-dimethoxy- 1,2,3,4-tetrahydro-1,3-thiazolo[4,3-a]isoquinoline are obtained; m.p. 229°–230° C.

EXAMPLE 19

20.0 g. of pyridine hydrochloride are added to 6.0 g. of 1-cyano-3-imino-8,9-dimethoxy-3,4,5,6-tetrahydro-1,3-thiazolo[4,3-a]isoquinoline hydrochloride, and the mixture is kept for 2 hours in an oil bath of 210°–220° C. The mixture is cooled and a mixture of 6 ml. of concentrated hydrochloric acid and 14 ml. of water is added. 5.2 g. of crystalline 1-cyano-3-imino-8,9-dihydroxy-3,4,5,6-tetrahydro-1,3-thiazolo[4,3-a]isoquinoline hydrochloride dihydrate are obtained; m.p.: gradually decomposes from 280° C. (after recryltallization from hot water).

Analysis: Calculated for $C_{12}H_{14}N_3O_4SCl$ (M: 331.78): C: 43.44%, H: 4.25%, N: 12.66%, Cl: 10.68%, S: 9.66%. Found: C: 43.84%, H: 4.37%, N: 12.26%, Cl: 10.66%, S: 10.03%.

EXAMPLE 20

1.0 g. of 1-cyano-8,9-dimethoxy-3,4,5,6-tetrahydro-1,3-thiazolo[4,3-a]isoquinoline-3-on is added in portions into 3 ml. of concentrated sulfuric acid with stirring. The reaction mixture is left to stand for 24 hours, thereafter it is poured onto ice. 0.75 g. of 1-carboxamide-8,9-dimethoxy-3,4,5,6-tetrahydro-1,3-thiazolo[4,3-a]isoquinoline-3-on are obtained; m.p.: 222°–224° C. (after recrystallization from 75% alcohol).

Analysis: Calculated for $C_{14}H_{14}N_3O_4S$ (M=306.33): C: 54.88%, H: 4.61%, N: 9.14%, S: 10.47%. Found: C: 54.65%, H: 4.41%, N: 9.38%, S: 10.50%.

EXAMPLE 21

120 ml. of 96% alcohol and 27.0 ml. of 10% sodium-hydroxide solution are added to 12.0 g. of S-(α-cyano-α-6,7-dimethoxy-3,4-dihydro-1-isoquinolyl)-methyl-isothiuronium bromide, and the mixture is refluxed for 2 hours. Thereafter 6.5 g. of ethyl chloroformate are added dropwise to the boiling mixture within 10 minutes, and the mixture is refluxed for an additional 0.5 hours. Upon cooling, 6.65 g. of 1-cyano-8,9-dimethoxy-3,4,5,6-tetrahydro-1,3-thiazolo[4,3-a]isoquinoline-3-on separates in crystalline state; m.p.: 205°–207° C. (after recrystallization from butanol).

EXAMPLE 22

To 4.0 g. of S-(α-cyano-α-6,7-dimethoxy-3,4-dihydro-1-isoquinolyl-methyl-isothiuronium-bromide 50 ml of 96% alcohol and 11.0 ml of 10% sodium hydroxide solution are added and the reaction mixture is refluxed. After 2 hours the refluxing solution is saturated with phosgene and refluxed for a further period of 30 minutes. On cooling 2.5 g of 1-cyano-8,9-dimethoxy-3,4,5,6-tetrahydro-1,3-thiazolo[4,3-a]isoquinoline-3-one crystallizes, the properties thereof being identical with the product obtained by example 6.

What is claimed is:
1. A compound of the formula:

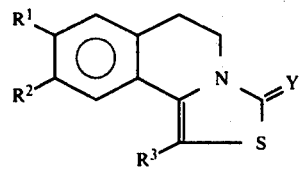

or a pharmaceutically acceptable salt thereof wherein $R^1$ and $R^2$ are methoxy;

R³ is hydrogen, methyl, nitro, phenyl, carboxy or carboxamido; and

Y is imino, oxo, sulfo, N-p-chlorophenylimino, acetimino, benzolylimino, or N-2-hydroxyethylimino.

2. The compound defined in claim 1 selected from the group consisting of:

3-imino-8,9-dimethoxy-3,4,5,6-tetrahydro-1,3-thioazolo (4,3a)iso-quinoline, or its rhodanide and hydrochloride;

1-carboxamido-3-imino-3,4,5,6-tetrahydro-3,9-dimethoxy-1,3-thiazolo(4,3a)isoquinoline;

1-methyl-3-imino-3,9-dimethoxy-3,4,5,6-tetrahydro-1,3-thiazolo(4,3a)isoquinoline and its rhodanide;

1-phenyl-3-imino-3,9-dimethoxy-3,4,5,6-tetrahydro-1,3-thiazolo(4,3a)isoquinoline and its rhodanide or hydrochloride;

1-carboxy-e-imino-3,9-dimethoxy-3,4,5,6-tetrahydro-1,3-thiazolo(4,3a)isoquinoline; and 1-carboxamido-3,9-dimethoxy-3,4,5,6-tetrahydro-1,3-thioazolo(4,3a)isoquinoline-3-one.

3. The compound defined in claim 2 selected from the group consisting of 1-carboxamido-3-imino-3,4,5,6-tetrahydro-8,9-dimethoxy-1,3-thiazolo-(4,3a)isoquinoline.

4. A method of treating angina in humans which comprises administering a compound as defined in claim 2 or a pharmaceutically acceptable salt thereof in a pharmaceutically effective dosage.

5. The method defined in claim 4 wherein the daily dosage is from 100γγ to 200γ/kg.

6. An antianginal composition for human or veterinary therapeutics containing as active ingredient an effective amount of the compound defined in claim 2 or a pharmaceutically acceptable salt thereof.

* * * * *

UNITED STATES PATENT AND TRADEMARK OFFICE
CERTIFICATE OF CORRECTION

PATENT NO. : 4,163,786
DATED : 7 August 1979
INVENTOR(S) : Kalman Harsanyi et al.

It is certified that error appears in the above-identified patent and that said Letters Patent are hereby corrected as shown below:

Col. 15, lines 11, 13 and 15, for "-3,9-dimethoxy" read

- - -8,9-dimethoxy - -; and

Col. 16, line 1, for "-e-imino-3,9-dimethoxy" read

- - -3-imino-8,9-dimethoxy - -.

Signed and Sealed this

Nineteenth Day of February 1980

[SEAL]

Attest:

SIDNEY A. DIAMOND

Attesting Officer

Commissioner of Patents and Trademarks